(12) United States Patent
Graebner (10) Patent No.: US 9,134,222 B1
(45) Date of Patent: Sep. 15, 2015

(54) SYSTEM AND METHOD FOR STRESS CORROSION TESTING

(71) Applicant: The Boeing Company, Chicago, IL (US)

(72) Inventor: Kim E. Graebner, Derby, KS (US)

(73) Assignee: The Boeing Company, Chicago, IL (US)

( * ) Notice: Subject to any disclaimer, the term of this patent is extended or adjusted under 35 U.S.C. 154(b) by 319 days.

(21) Appl. No.: 13/849,958

(22) Filed: Mar. 25, 2013

(51) Int. Cl.
*G01N 17/00* (2006.01)
*G01N 3/08* (2006.01)

(52) U.S. Cl.
CPC .............. *G01N 17/002* (2013.01); *G01N 3/08* (2013.01)

(58) Field of Classification Search
CPC .............. G01N 17/00; G01N 17/002; G01N 2203/0062; G01N 3/20; G01N 3/567; G01N 3/08; G01N 3/28
USPC ............................................................ 73/86
See application file for complete search history.

(56) References Cited

U.S. PATENT DOCUMENTS

| | | | | |
|---|---|---|---|---|
| 3,224,266 A * | 12/1965 | Klippert | ................ | 73/150 R |
| 3,504,535 A * | 4/1970 | Cobb et al. | ................ | 73/86 |
| 3,936,273 A * | 2/1976 | Powell | ................ | 422/53 |
| 4,282,181 A | 8/1981 | Pierce | | |
| 4,689,472 A * | 8/1987 | Singleton et al. | ........... | 392/405 |
| 4,698,507 A * | 10/1987 | Tator et al. | .............. | 250/429 |
| 4,711,131 A * | 12/1987 | Hopkins | .............. | 73/799 |
| 5,039,228 A * | 8/1991 | Chalmers | .............. | 374/57 |
| 7,141,150 B1 * | 11/2006 | Welch et al. | .............. | 204/401 |
| 7,313,976 B2 * | 1/2008 | Swain et al. | .............. | 73/865.6 |
| 7,387,031 B1 * | 6/2008 | Perrin et al. | .............. | 73/820 |
| 8,261,601 B2 * | 9/2012 | Stolle et al. | .............. | 73/86 |
| 2006/0070452 A1* | 4/2006 | Bohlmann et al. | .............. | 73/800 |
| 2012/0024433 A1 | 2/2012 | Yanar et al. | | |

OTHER PUBLICATIONS

National Physical Laboratory, "Stress Corrosion Cracking," 1982.
ASTM International, "ASTM G44," 2013.
ASTM International, "ASTM G39," 1999.
ASTM International, "ASTM G36," 2013.

* cited by examiner

*Primary Examiner* — Freddie Kirkland, III (57) ABSTRACT

A testing apparatus may include a reservoir and a test tank. The reservoir may contain a solution. The test tank may contain a test specimen for stress corrosion testing. A fill pump may pump the solution from the reservoir to the test tank. A sequence controller may be communicatively coupled to the fill pump and may provide sequence timing to control an immersion time period and a drying time period of the test specimen.

17 Claims, 7 Drawing Sheets

SYSTEM AND METHOD FOR STRESS CORROSION TESTING

The invention described herein was made in the performance of work under Department of Defense Contract No. FA8107-09-D-0001 and is subject to the provisions of Section 305 of the National Aeronautics and Space Act of 1958 (72 Stat. 435: 42 U.S.C. 2457).

FIELD

The present disclosure relates generally to material testing and, more particularly, to the testing of materials for susceptibility to stress corrosion cracking.

BACKGROUND

Stress corrosion cracking is a phenomenon that occurs in certain materials when placed in a stressed state and exposed to a corrosive environment. The stressed state may include a state wherein the material is subjected to tensile stress. Tensile stress may include residual stress occurring in the material as a result of a manufacturing process such as machining, welding, and/or heat-treating the material. Tensile stress in the material may also result from an externally-applied load such as a sustained load or a cyclic load applied to the material in its normal operating environment.

Corrosive environments that can lead to stress corrosion cracking include environments where the material is exposed to water vapor or an aqueous solution. The occurrence of stress corrosion cracking is highly dependent on the chemical makeup of the environment and the composition of the material. Materials that are susceptible to stress corrosion cracking include metallic materials (e.g., aluminum, stainless steel and other ferrous alloys), polymeric materials (e.g., polycarbonates, polyesters), and other materials. The occurrence of stress corrosion cracking is also highly dependent on the temperature and relative humidity of the surrounding environment. Stress corrosion cracking may occur as intergranular cracks that penetrate from the surface into the depth of the material. The cracks may be microscopic in size making detection difficult. In addition, the surface of the material may appear to be unaffected which may increase the difficulty of detecting stress corrosion cracking.

Testing a material for susceptibility to stress corrosion cracking may be performed at an accelerated rate under a set of testing requirements published by the American Society of Testing Materials (ASTM). ASTM G-44 provides for accelerated testing of metallic materials by alternate immersion of a test specimen in a 3.5% NaCl solution. ASTM G-44 includes relatively stringent requirements for controlling the temperature and relative humidity of the environment to which a test specimen is subjected, and for controlling the volume of the corrosive solution relative to the test specimen surface area immersed in the corrosive solution. ASTM G-44 additionally provides for the option of inducing tensile stress in a test specimen during alternate immersion testing. Tensile stress may be induced in a material up to a percentage of the material yield strength, and which may be representative of the stress to which the material may be subjected in its service environment.

The prior art includes several methods for alternate immersion testing of a material for evaluating stress corrosion cracking One prior art method uses a Ferris wheel arrangement having trays containing test specimens which are rotated through a corrosive solution. Unfortunately, the Ferris wheel arrangement lacks the ability to control the immersion time period of the test specimens independent of the drying time period due to the dependence of the immersion and drying time period on the depth of the solution and the rotational speed of the wheel. If the rotational speed of the wheel is decreased to provide a longer immersion time period, then the drying time period is increased. If the solution depth is increased to provide a longer immersion time period, then the drying time period is reduced. Another prior art method provides a means for alternate immersion testing of test specimens. However, the method lacks the ability to control the testing environment in accordance with the stringent temperature and humidity requirements of ASTM G-44.

As can be seen, there exists a need in the art for a system and method of alternate immersion testing of a test specimen for stress corrosion cracking susceptibility which provides a means for altering the immersion time period independent of the drying time period. In addition, there exists a need in the art for a system and method for alternate immersion testing of a test specimen for stress corrosion cracking susceptibility which provides a means for controlling the temperature and humidity of the environment to which a test specimen is subjected.

SUMMARY

The above-noted needs associated with stress corrosion testing are specifically addressed and alleviated by the present disclosure which provides a testing apparatus which may include a reservoir and a test tank. The reservoir may contain a solution. The test tank may contain a test specimen for stress corrosion testing. A fill pump may pump the solution from the reservoir to the test tank to immerse the test specimen in the solution for a predetermined immersion time period after which the test tank may be drained of solution to allow the test specimen to dry during a predetermined drying time period. A sequence controller may be communicatively coupled to the fill pump and may provide sequence timing to control the immersion time period and the drying time period of the test specimen.

In a further embodiment, disclosed is a testing apparatus that may include a reservoir configured to contain a solution, and a test tank fluidly coupled to the reservoir. The test tank may be positioned above the reservoir, and may be configured to contain a test specimen and receive the solution from the reservoir for immersion of the test specimen. The testing apparatus may include a fill pump configured to pump the solution from the reservoir up to the test tank. The test tank may include a drain valve for draining the solution into the reservoir by gravity feed. The testing apparatus may further include a sequence controller communicatively coupled to the fill pump and the drain valve. The sequence controller may be configured to provide sequence timing to control an immersion time period and a drying time period of the test specimen.

Also disclosed is a method of stress corrosion testing of a test specimen. The method may include fixedly positioning a test specimen in a test tank, and pumping the solution from the reservoir into the test tank. The method may further include immersing the test specimen within the solution for an immersion time period, and allowing the test specimen to dry for a drying time period. The method may further additionally include circulating, using an air conditioning system, air within the test tank during the immersion time period and/or the drying time period.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
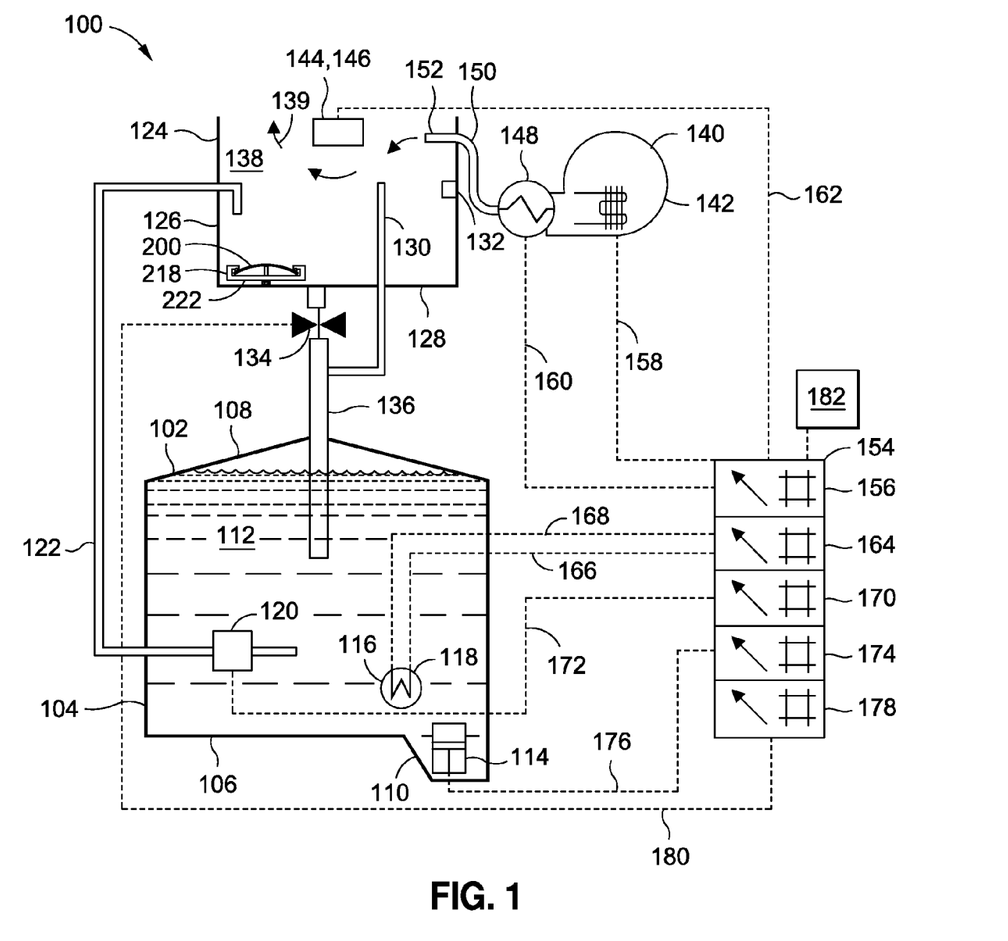
FIG. 1 is a schematic diagram of an embodiment of a testing apparatus for stress corrosion testing of a test specimen.

Referring now to the drawings wherein the showings are for purposes of illustrating preferred and various embodiments of the disclosure, shown in FIG. 1 is a diagram of an embodiment of a testing apparatus 100 that may be implemented for evaluating the stress corrosion cracking susceptibility of one or more test specimens 200. The testing apparatus 100 advantageously provides a means for evaluating the stress corrosion behavior of a material in a specific environment for an accelerated time that may be representative of the in-service environment of the material. In this regard, the testing apparatus 100 provides a means for determining the amount of time required for stress corrosion cracking to develop in a material, and provides a means to correlate the extent and nature of such stress corrosion cracking to air temperature, relative humidity, composition and temperature of the corrosive environment (i.e., solution), tensile stress level in the material, and other testing parameters that may be representative of the in-service environment of the material.

Advantageously, the testing apparatus 100 provides a simple and cost-effective means for fulfilling all of the requirements of ASTM G-44 including controlling the immersion time period independent of the drying time period, and accurately controlling the air temperature and the relative humidity of the testing environment. Furthermore, the testing apparatus 100 provides a means for testing any number of test specimens 200 simultaneously, and may run unattended for extended periods of time such as for days or weeks. The testing apparatus 100 may be used in conjunction with a simple mechanical stressing fixture 222 (FIG. 4) to apply tensile stress 212 (FIG. 4) to a test specimen 200 to simulate the loading condition of the material in service. The testing apparatus 100 may be used for stress corrosion cracking testing and/or exfoliation corrosion testing of test specimens formed of any material, without limitation, including specimens formed of metallic material, polymeric material, ceramic material, or any combination of materials.

In FIG. 1, the testing apparatus 100 may include a reservoir 102 fluidly coupled to a test tank 124. The reservoir 102 may contain a corrosive solution 112. The test tank 124 that may be located above the reservoir 102 and may be configured to contain one or more test specimens 200. Under the control of a sequence controller 154, the test tank 124 may be alternately filled and drained to alternately immerse the test specimen 200 in the solution 112, and then allow the test specimen 200 to dry over a repeated number of immersion/drying cycles. The number of immersion/drying cycles may continue uninterrupted over an extended time period (e.g. 1 day, 2 days, 10 days, 90 days, etc.) depending on the relative susceptibility of the material being tested and the intended service environment.

The reservoir 102 may include reservoir side walls 104 and a reservoir bottom wall 106 which may optionally include a sump 110 for mounting a circulation pump 114 as described below. The reservoir 102 may optionally include a reservoir top wall 108 for the enclosing the reservoir 102 and which may optionally be formed in a conical shape. In this regard, the reservoir 102 may be provided in any size, shape, and configuration, without limitation, including a cylindrical shape or an orthogonal shape. The reservoir 102 may be formed of a material that is inert to attack by the corrosive solution 112. For example, the reservoir 102 may be formed of inert plastic such as polyethylene, glass, metallic material such as stainless steel, or any other material that is inert to the solution 112. The solution 112 may be provided in a chemical composition that may simulate the in-service environment of the material. In an embodiment, the solution 112 may comprise an aqueous chloride solution such as a 3.5% sodium chloride (NaCl) solution. The solution 112 may be provided with a predetermined pH range such as a pH range of between approximately 6.4 to 7.2, although the solution 112 may be provided in any pH range.

In FIG. 1, the reservoir 102 may be sized to contain a volume of solution 112 that allows for a predetermined time period of unattended operation such that the test specimen 200 may be subjected to the intended number of immersion/drying cycles without interruption and/or in accordance with the requirements of ASTM G-44. For example, the reservoir 102 may be provided in a size for containing a volume of solution 112 allowing for at least ten (10) days of unattended operation at a time. In an embodiment, the reservoir 102 may be sized to contain 100 gallons or more of solution 112. In addition, the reservoir 102 may be sized to contain a volume of solution 112 that prevents a change in the concentration of the corrosive solution 112 greater than a predetermined amount in consideration of evaporation that may continuously occur during testing. For example, the reservoir 102 may be sized to contain a volume of solution 112 that prevents a change in the concentration of greater than approximately 1% from the initial concentration due to evaporation.

The testing apparatus 100 may include a circulation pump 114. The circulation pump 114 may be mounted in the sump 110 of the reservoir 102 and may be configured to circulate or agitate the solution 112 to maintain a substantially uniform concentration for composition of the solution 112 throughout the reservoir. For an NaCl solution 112, the circulation pump 114 may circulate or agitate the solution 112 to maintain a substantially uniform salt concentration throughout the volume of solution 112 contained within the reservoir 102. In this manner, the circulation pump 114 may prevent a change in the concentration of the corrosive solution 112 during the testing duration. In an embodiment, the operation of the circulation pump 114 may be controlled by a circulation pump controller 174 which may comprise part of a sequence controller 154. The circulation pump controller 174 may be communicatively coupled to the circulation pump controller 174 by a circulation pump signal line 176. The circulation pump controller 174 may activate the circulation pump 114 for a predetermined period of time (e.g., for 1 minute) prior to initiating a fill pump 120 for filling of the test tank 124 with solution 112 as described below.

In FIG. 1, the testing apparatus 100 may include a reservoir thermocouple 116 that may be mounted in the reservoir 102 for measuring a temperature of the solution 112. The reservoir thermocouple 116 may be communicatively coupled to a reservoir heater controller 164 via a thermocouple signal line 168. The testing apparatus 100 may further include a solution heater 118 that may be mounted to or contained within the reservoir 102 for heating the solution 112. The solution heater 118 may be coupled to the reservoir heater controller 164 by a reservoir heater signal line 166. The reservoir heater controller 164 may maintain the solution 112 within a desired solution temperature range depending upon solution temperature measurements provided by the reservoir thermocouple 116. However, in an embodiment of the testing apparatus 100, the solution 112 may be non-heated, and may be allowed to come to an equilibrium temperature upon exposure to the air 138 in the testing environment and wherein the air temperature and relative humidity in the test tank 124 or testing environment may be controlled by an air conditioning system 140 and/or by an air heater 148 as described in greater detail below.

The testing apparatus 100 may further include a fill pump 120 that may be configured to pump solution 112 from the reservoir 102 up to the test tank 124. The fill pump 120 may be mounted to the reservoir 102 or in the reservoir 102 and may be coupled to a fill pipe 122 fluidly extending from the reservoir 102 to the test tank 124. The fill pipe 122 may terminate at the test tank 124 and may discharge solution 112 into the test tank 124 as shown in FIG. 1. Advantageously, the fill pump 120 may be controlled or regulated by a fill pump controller 170 that may be communicatively coupled to the fill pump 120 by a fill pump signal line 172. The fill pump controller 170 may alternately activate and deactivate the fill pump 120 to allow for independent control of the immersion time period and the drying time period of the test specimen 200 in the test tank 124.

In an embodiment, the fill pump 120 may be configured to pump solution 112 into the test tank 124 such that the test specimen 200 may be completely immersed in the solution 112 within a predetermined amount of time. For example, the fill pump 120 may be configured to pump solution 112 into the test tank 124 such that the test specimen 200 is immersed in solution 112 within approximately two (2) minutes elapsed time from when a first portion of the test specimen 200 is contacted by the solution 112 until the test specimen 200 is fully covered by the solution 112, according to the requirements of ASTM G-44. In an embodiment, the fill pump 120 may be configured such that the test specimen 200 is completely immersed in solution 112 within an elapsed time of approximately 40 seconds of when the test specimen 200 initially comes into contact with the solution 112. The fill pump 120 may have a pumping capacity of up to approximately 50 gallons of solution 112 per minute or greater, although the fill pump 120 may be provided in any pumping capacity. The pumping capacity of the fill pump 120 may be selected to meet the above-noted requirements for completely immersing the test specimen 200 within approximately two (2) minutes from when a first portion of the test specimen 200 is contacted by the solution 112, per ASTM G-44

In FIG. 1, the testing apparatus 100 may include the test tank 124 which may be configured to contain at least one test specimen 200. The test tank 124 may be provided in a size that meets the minimum requirements of ASTM G-44 regarding volume of solution 112 relative to total surface area of the test specimen(s) 112 in the test tank 124. In this regard, the test tank 124 may be provided in a size that holds a volume of solution 112 relative to the test specimen surface area of at least 32 mL/cm$^2$ (or 200 mL/in$^2$). The test tank 124 may include tank side walls 126 and a tank bottom wall 128. Optionally, the test tank 124 may include a top wall (not shown) to enclose the test tank 124 interior which may improve the ability to control the air temperature and the relative humidity of the air 138 within the test tank 124. The tank side walls 126 and tank bottom wall 128 may be formed of a material that is inert to the corrosive solution 112. The material from which the test tank 124 is formed may be the same material or substantially similar material from which the reservoir 102 may be formed as mentioned above.

In an embodiment, the test tank 124 may be configured to contain multiple test specimens 200. The test specimens 200 may preferably be formed of the same material (e.g., same alloy) to avoid cross-contamination. In an embodiment, the test specimens 200 may be supported on a test rack or specimen holder 218 such as a shelf that may be mounted to the test tank 124 or integrally formed with the test tank 124. In a further embodiment, the specimen holder 218 (FIG. 3) may comprise a standalone structure that may be removed from the test tank 124 to allow for mounting of one or more test specimens 200 on the specimen holder 218, as mentioned below. In a further embodiment, that specimen holder 218 may comprise a stressing fixture 222 (FIG. 4) for inducing or applying tensile stress to the test specimen 200 as described in greater detail below.

In FIG. 1, the test tank 124 may receive the solution 112 from the reservoir 102 via the fill pipe 122 under the pumping action of the fill pump 120. The fill pipe 122 may penetrate the test tank side wall 126 and discharge solution 112 from a terminal end of the fill pipe 122 into the test tank 124. The fill pump controller 170 may be programmed to activate the fill pump 120 such that the fill pump 120 continues to pump solution 112 into the test tank 124 for a predetermined time period (e.g., 50 seconds) which may correspond to the amount of time required to fully immerse all of the test specimens 200 in the test tank 124. However, the test tank 124 may include an automatic fill switch 132 which may be activated upon the solution 112 reaching a predetermined fill level (not shown) within the test tank 124. The automatic fill switch 132 may send a signal to the fill pump controller 170 causing the fill pump controller 170 to turn off or deactivate the fill pump 120 if the predetermined fill level is reached prior to the expiration of the predetermined time period (e.g., 50 seconds). The test tank 124 may also include an overflow pipe 130 for draining solution 112 from the test tank 124 when the solution 112 level is at an upper end of the overflow pipe 130 as protection against overfilling the test tank 124.

The test tank 124 may include a drain valve 134 that may be mounted in the tank bottom wall 128. The drain valve 134 may be coupled to or mounted in a drain pipe 136 fluidly connecting the test tank 124 to the reservoir 102 and configured to allow the solution 112 to drain from the test tank 124 and into the reservoir 102. The drain valve 134 may be air-actuated, electrically-actuated, or actuated by alternative means. The drain valve 134 may be coupled to a drain valve controller 178 via a drain valve signal line 180. Prior to activating the fill pump 120 for filling the test tank 124 with the solution 112, the drain valve controller 178 may close the drain valve 134. The drain valve 134 may remain closed for the duration of the test specimen immersion time period, after which the drain valve 134 may be opened by the drain valve controller 178. With the drain valve 134 open, the solution 112 may drain under gravity feed back into the reservoir 102 until the test tank 124 is empty.

Figure 2:
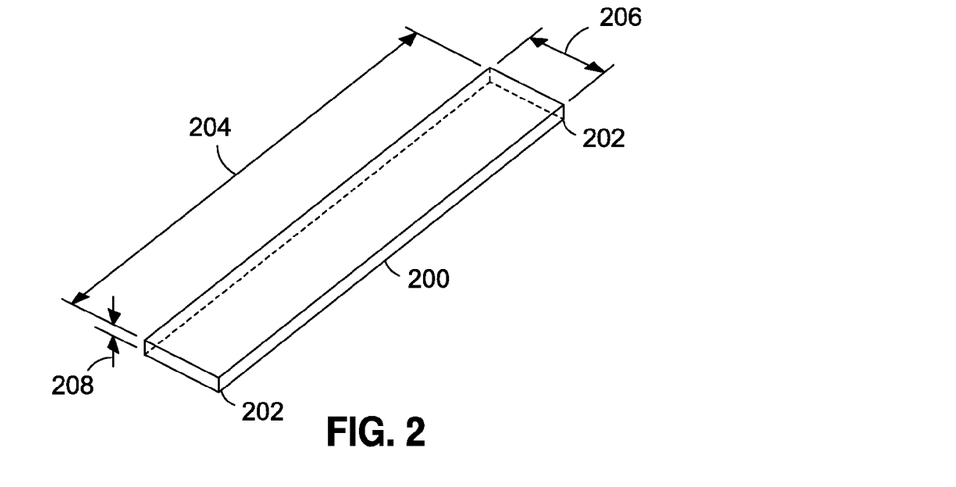
FIG. 2 is a perspective illustration of a test specimen for testing in the testing apparatus.

Referring to FIG. 2, shown is an embodiment of a test specimen 200 which may be provided as a generally elongated strip having a generally flat or planar configuration. The test specimen 200 may be formed of material representing the in-service material to be evaluated for stress corrosion cracking susceptibility. As indicated above, the test specimen 200 may be formed of any material including, but not limited to, metallic material, polymeric material, ceramic material, or any one of a variety of other materials. In an embodiment, the test specimen 200 may be formed of aluminum of any alloy and heat-treat specification (e.g., 7075-T6).

In FIG. 2, the test specimen 200 is shown having a generally elongated configuration. For example, the test specimen 200 may be provided in a test specimen thickness 208 of approximately 5-6 millimeters (mm), a test specimen width 206 of approximately 15-25 mm, and a test specimen length 204 of approximately 150 mm. Such elongated configuration may be suitable for mounting the test specimen 200 in a stressing fixture 222 to induce tensile stress in the test specimen 200. However, the test specimen 200 may be provided in any size, shape and configuration, without limitation.

Figure 3:
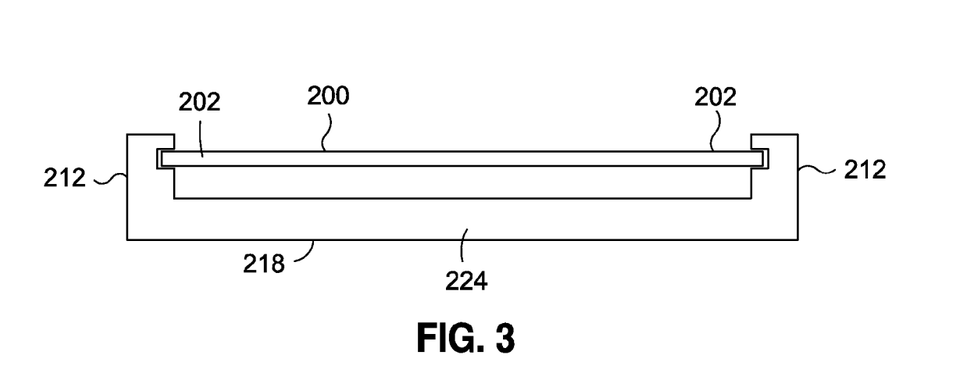
FIG. 3 is an illustration of an embodiment of a specimen holder for mounting the test specimen in a test tank of the testing apparatus.

Referring to FIG. 3, shown is a specimen holder 218 for fixedly positioning one or more test specimens 200 in the test tank 124. In an embodiment, the specimen holder 218 may include a fixture base 224 having a pair of standoffs 220 extending upwardly from the fixture base 224. The standoffs 220 may have notches formed complementary to the test specimen thickness 208. The standoffs 220 may be formed of a material (e.g., ceramic material) that minimizes or eliminates the occurrence of galvanic corrosion between the test specimen 200 and the standoffs 220. The specimen holder 218 may be configured to minimize overlap of the specimen holder 218 with the surface area of the test specimen 200.

Referring to FIG. 3, shown is an embodiment of a specimen holder 218 configured as a stressing fixture 222. In an embodiment for simultaneous testing of multiple test specimens 200, each one of the test specimens 200 may be smoothly machined before mounting in the stressing fixture 222 to equalize any residual stress imparted by the machining operation into the test specimens 200. For simultaneous testing of multiple test specimens 200, the test specimens 200 are preferably formed of the same alloy to avoid contamination of the solution 112 and improve the accuracy of the test.

The stressing fixture 222 may be configured to induce tensile stress 212 in the test specimen 200 up to a predetermined threshold value. In an embodiment, the stressing fixture 222 may be configured as a mechanical plate-stressing fixture 222 for applying tensile stress 212 to the test specimen 200. In the embodiment shown, the stressing fixture 222 may comprise a bent-beam fixture having a fixture base 224 and opposing fixture sidewalls 226 coupled to the fixture base 224. Each one of the fixture sidewalls 226 may include a lip 228 having a cylindrical end support 230. The end supports 230 may constrain the opposing specimen ends 202 of the test specimen 200. The stressing fixture 222 may further include an axially adjustable (e.g., threaded) tensioning bolt 232 extending upwardly through the fixture base 224. The tensioning bolt 232 may be located approximately midway between the opposing end supports 230 and may be axially movable to induce out-of-plane bending in the test specimen 200 within the elastic limits thereof, and resulting in substantially uniform tensile stress 212 over a relatively large area on a convex side 210 of the test specimen 200 and compression stress 216 on a concave side 212 of the test specimen 200.

Referring back to FIG. 1, the testing apparatus 100 may include an air conditioning system 140 that may be fluidly coupled to the test tank 124. The air conditioning system 140 may be configured to control an air temperature and a relative humidity of air circulation 139 in the test tank 124. In an embodiment, the air circulation 139 may be controlled to the ASTM G-44 specified air temperature limits and relative humidity limits. For example, in an embodiment, the air conditioning system 140 may be configured to maintain the air temperature at approximately 27 C±1 C and maintain the relative humidity at approximately 45%±10%. The air conditioning system 140 may be configured to continuously circulate the air 138 in the test tank 124 to maintain a uniform rate of drying of the test specimens 200 and/or a uniform rate of evaporation of test solution 112.

In FIG. 1, in an embodiment, the air conditioning system 140 may include a compressor 142 that may be coupled to an evaporator coil and a condenser. The air conditioning system 140 may be fluidly coupled to the test tank 124 by a duct 150 having a duct outlet 152 terminating inside the test tank 124. The air conditioning system 140 may further include an air heater 148 such as an inline duct heater fluidly coupled to the air duct 150 and configured to heat the air 138 in the test tank 124. In an embodiment, the air conditioning compressor 142 and the inline duct heater may be independently regulated by an air conditioning controller 156 and a duct heater signal line 160 for regulating the air temperature and the humidity level within the test tank 124 and/or within a room containing the testing apparatus 100.

The air conditioning system 140 may further include a tank thermocouple 144 that may be mounted in the test tank 124. The tank thermocouple 144 may be configured to measure the air temperature in the test tank 124 when the solution 112 is drained therefrom. The air conditioning system 140 may additionally include a hydrometer 146 that may be mounted in the test tank 124 and configured to measure the relative humidity of the air 138. The tank thermocouple 144 and the hydrometer 146 may be communicatively coupled to the air conditioning controller 156 via an air conditioning-hydrometer signal line 162. The air conditioning controller 156 may rely on measurements of air temperature and relative humidity from the tank thermocouple 144 and the hydrometer 146 to regulate the operation of the air conditioning compressor 142 and the air heater 148 to maintain the air temperature in the test tank 124 within the desired environmental parameters. For example, the air conditioning controller 156 may be programmed to maintain the environmental parameters within the above-mentioned requirements of ASTM G-44.

In FIG. 1, the testing apparatus 100 may comprise the sequence controller 154 which may include the fill pump controller 170 and the drain valve controller 178 and which may be communicatively coupled to the fill pump 120 and the drain valve 134, respectively, and provide sequence timing to control the immersion time period and the drying time period of the test specimen 200 in the test tank 124. Advantageously, the sequence controller 154 may control the immersion time period and the drying time period independently of one another. Furthermore, the sequence controller 154 may control the immersion time period and the drying time period in predetermined time intervals that may range from seconds to years (e.g., 10 years or more). In addition, the sequence controller 154 may include the reservoir heater controller 164 which may be communicatively coupled to the reservoir thermocouple 116 for receiving temperature measurements of the solution temperature for regulating the operation of the solution heater 118 mounted in the reservoir 102. Furthermore, the sequence controller 154 may include the air conditioning controller 156 which may receive input from the tank thermocouple 144 and the hydrometer 146 for controlling the air conditioning system 140 and the air heater 148 to regulate the air temperature and the relative humidity of the air 138 in the test tank 124.

In a further embodiment, the sequence controller 154 may be configured to record measurements of the test parameters. For example, the sequence controller 154 may be configured to record measurements of the air temperature and the relative humidity within the test tank 124 or the ambient environment of the location of the testing apparatus 100. For example, The sequence controller 154 may record test parameters such as solution temperature, test tank fill time, test specimen immersion time period, test tank drain time, test specimen drying time period, number of immersion-drying cycles, and other parameters. The sequence controller 154 may further be configured to chart or plot the measurement of such test parameters such as on a display monitor (not shown).

In FIG. 1, the sequence controller 154 may be configured to record such measurements at programmed intervals. In an embodiment, the sequence controller 154 may be configured to internally hold measurements for at least five (5) months or more of testing at a time. Such air temperature measurements and relative humidity measurements may be used for real-time charting of the testing progress. The sequence controller 154 software may be written to allow test operators to vary any one of a variety of testing parameters including, but not limited to, air temperature set point, relative humidity set point, circulation pump duration, immersion time period, drying time period, and immersion/drying cycle start and stop.

The sequence controller 154 may maintain the air temperature and the relative humidity within preprogrammed ranges and may be configured to send an alert upon the occurrence of an anomaly in the test measurements or testing parameters. For example, the sequence controller 154 may be configured to send an alarm signal, a text message, a voicemail, a visual signal (e.g., a flashing light or a continuous light) to personnel (e.g., to a computer or mobile telephone) if the testing apparatus 100 experiences an alarm condition. In an embodiment, the sequence controller 154 may include an alerting mechanism 182 that may be communicatively coupled to the sequence controller 154. The alerting mechanism 182 may be configured to autonomously transmit an alert upon the occurrence of an anomaly in the test measurements or testing parameters. For example, the alerting mechanism 182 may be configured to dial a wireless number or land-based phone number, send a text message, an email, a web service communication, or other communications, in the event of a test parameter anomaly.

The components of the testing apparatus 100 may be fixedly coupled together such as by mounting to a frame (not shown) and/or by mechanically coupling the components by welding and/or mechanically fastening. For example, the reservoir 102 and the test tank 124 may be coupled to one another by welding. The air conditioning system 140 may be coupled to the test tank 124 and the sequence controller 154 may be coupled to the reservoir 102.

Figure 5:
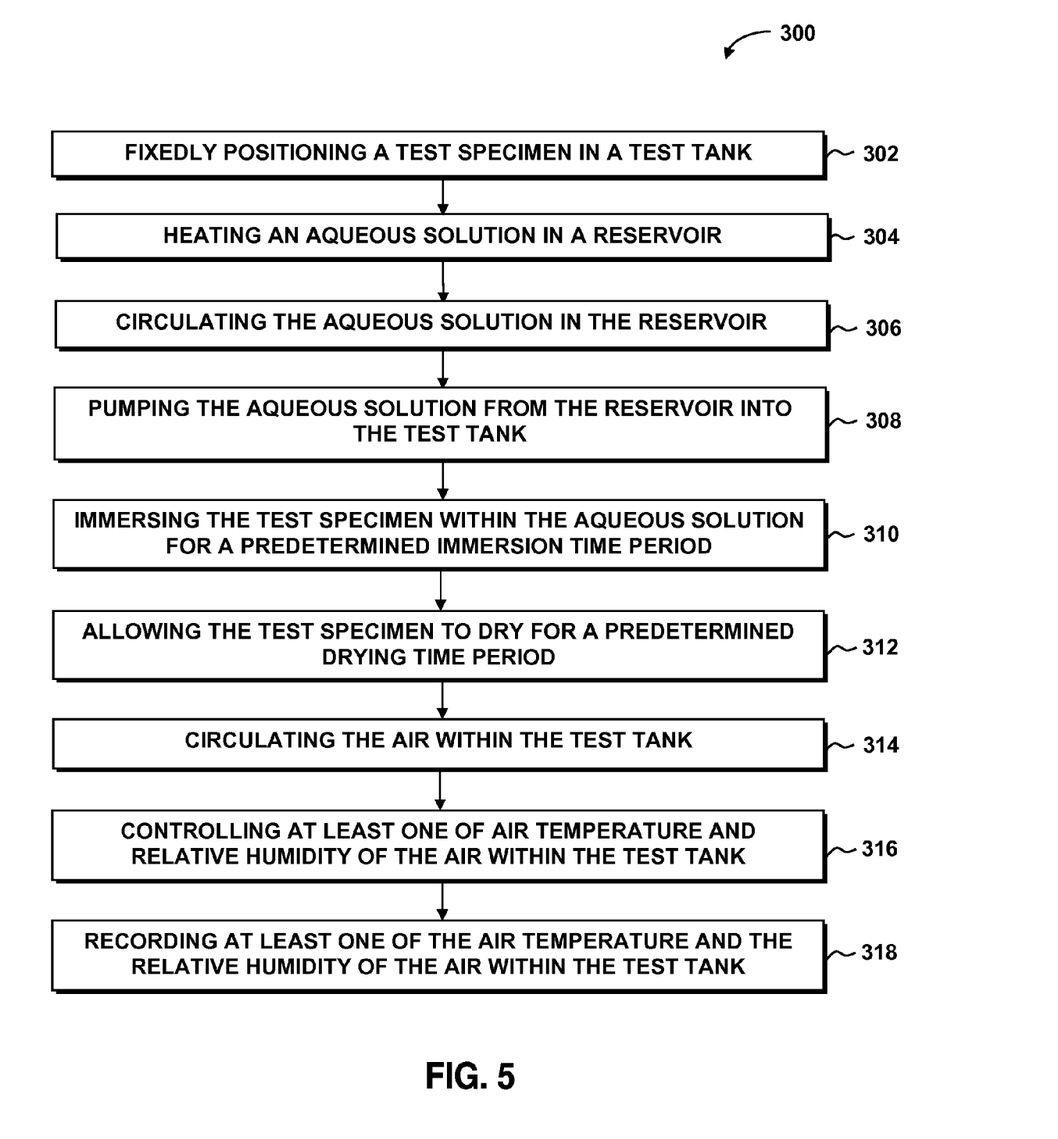
FIG. 5 is a flow chart illustrating one or more operations that may be included in a method of stress corrosion testing.

In FIG. 5, shown is an embodiment of a method 300 of stress corrosion testing of one or more test specimens 200. The method may include Step 302 comprising fixedly positioning a test specimen 200 in a test tank 124. The method may include closing a drain valve 134 located at the bottom of the test tank 124. The air conditioning system 140 may be activated to initiate air circulation 139 within the test tank 124 and/or in the environment containing the testing apparatus 100.

Step 304 of the method 300 of FIG. 5 may include heating the solution 112 in the reservoir 102 to a desired solution temperature. For example, the reservoir thermocouple 116 may transmit a solution temperature measurement to the reservoir heater controller 164. If the solution temperature is below a predetermined value (e.g. below 27 C), the solution heater 118 may be activated by the reservoir heater controller 164 until the solution 112 is heated to the desired temperature. However, in accordance with the requirements of ASTM G-44, the solution 112 may be non-heated and may be allowed to come to within a predetermined range (e.g., ±3 C) of room temperature or the temperature of the air 138 in the testing environment or test tank 124 prior to pumping the solution 112 into the test tank 124.

Step 306 of the method 300 of FIG. 5 may include circulating the solution 112 in the reservoir 102 using the circulation pump 114 mounted within the reservoir 102. As indicated above, the circulation pump 114 may circulate the solution 112 in the reservoir 102 to maintain a uniform concentration of the solution 112. Although not shown, the reservoir 102 may conclude one or more pH sensors to assess and compare the relative concentration level of the solution 112 at different locations in the reservoir 102. The circulation pump 114 may be activated as necessary to minimize differences or changes in the concentration of the solution 112 prior to pumping the solution 112 into the test tank 124.

Figure 6:
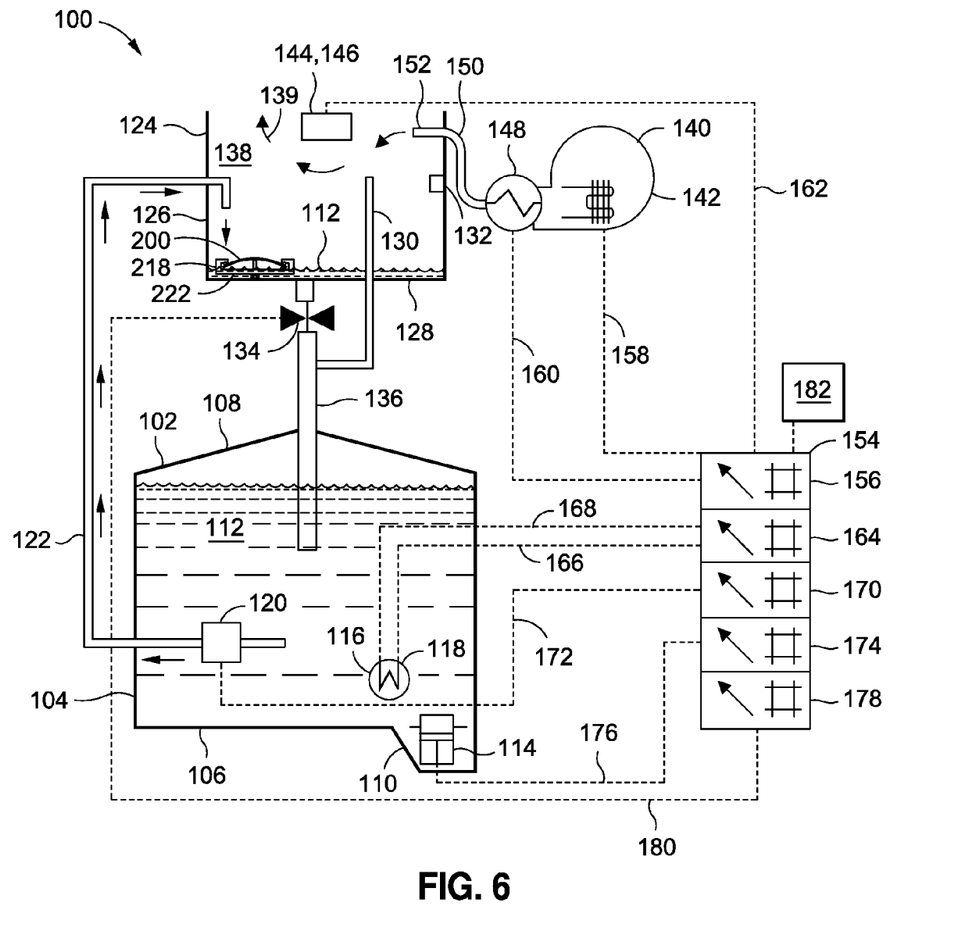
FIG. 6 is a schematic diagram of the testing apparatus of FIG. 1 illustrating the pumping of solution into a test tank which is positioned above a reservoir containing solution.

Step 308 of the method 300 of FIG. 5 may include pumping the solution 112 from the reservoir 102 into the test tank 124 as shown in FIG. 6. In an embodiment, the fill pump controller 170 may be programmed to activate the fill pump 120 such that the test specimen 200 is immersed within approximately two (2) minutes elapsed time from initial contact with solution 112 until the test specimen 200 is fully covered with solution 112. The test pump may be deactivated when the solution 112 reaches a predetermined level. In an embodiment, the method may include detecting a fill level of the test tank 124 using an automatic fill switch 132, and stopping the pumping of solution 112 into the test tank 124 when the solution 112 reaches a predetermined level.

Figure 7:
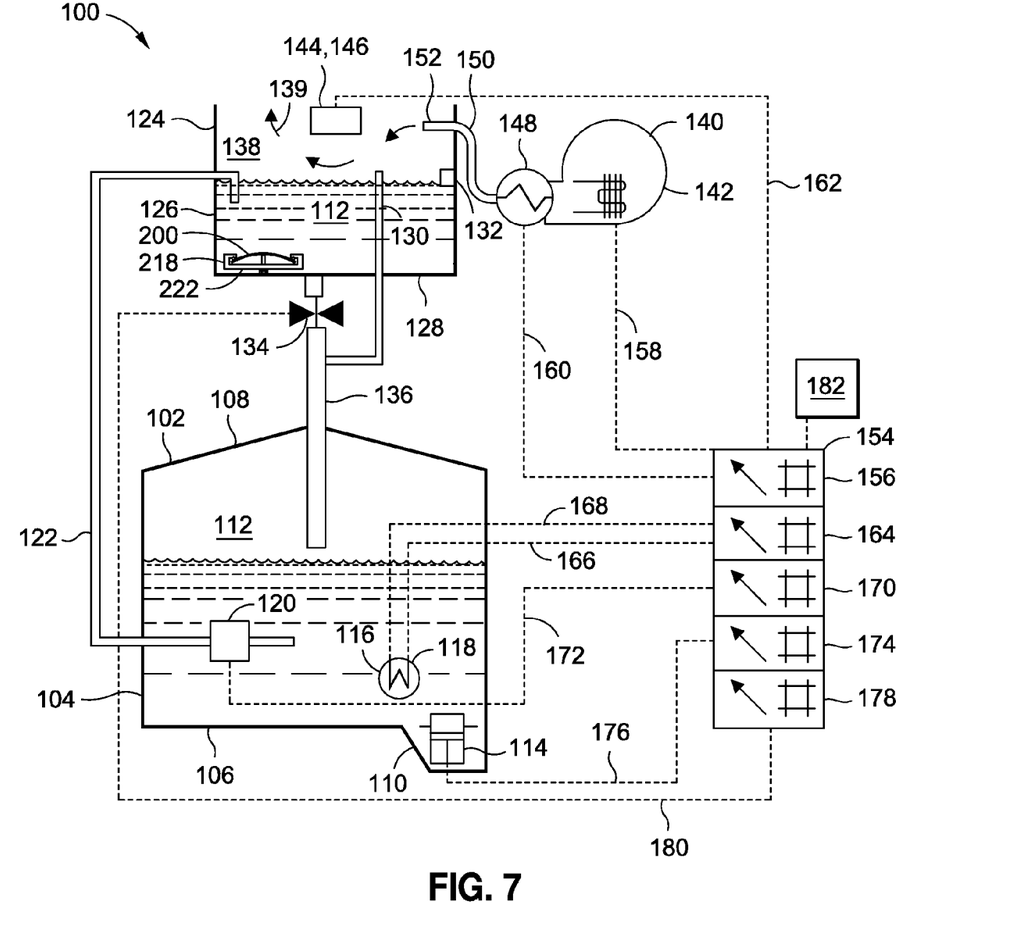
FIG. 7 is a schematic diagram of the testing apparatus illustrating the test tank in a filled state and the test specimen immersed in the solution.

Step 310 of the method 300 of FIG. 5 may include immersing the test specimen 200 within the solution 112 as shown in FIG. 7. The test specimen 200 may be immersed within the solution 112 for a predetermined immersion time period. For embodiments where the test specimen 200 is immersed according to ASTM G-44, the immersion time period may extend for 10 minutes of each hour±1 minute. However, the test specimen 200 may be immersed for any period time depending on the susceptibility to stress corrosion cracking and the extent to which the material will be exposed to corrosive chemicals when placed in its intended service environment.

Figure 8:
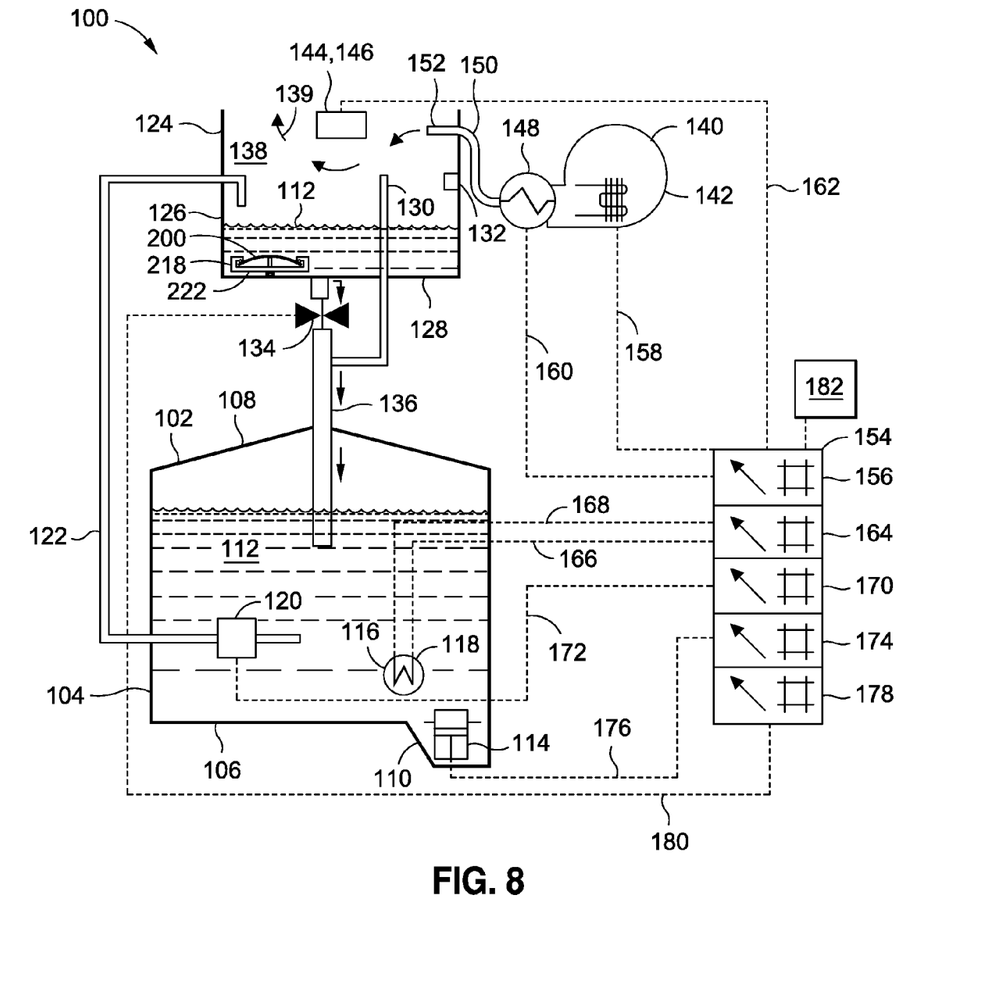
FIG. 8 is a schematic diagram of the testing apparatus illustrating the draining of the solution from the test tank to allow the test specimen to dry.
Figure 9:
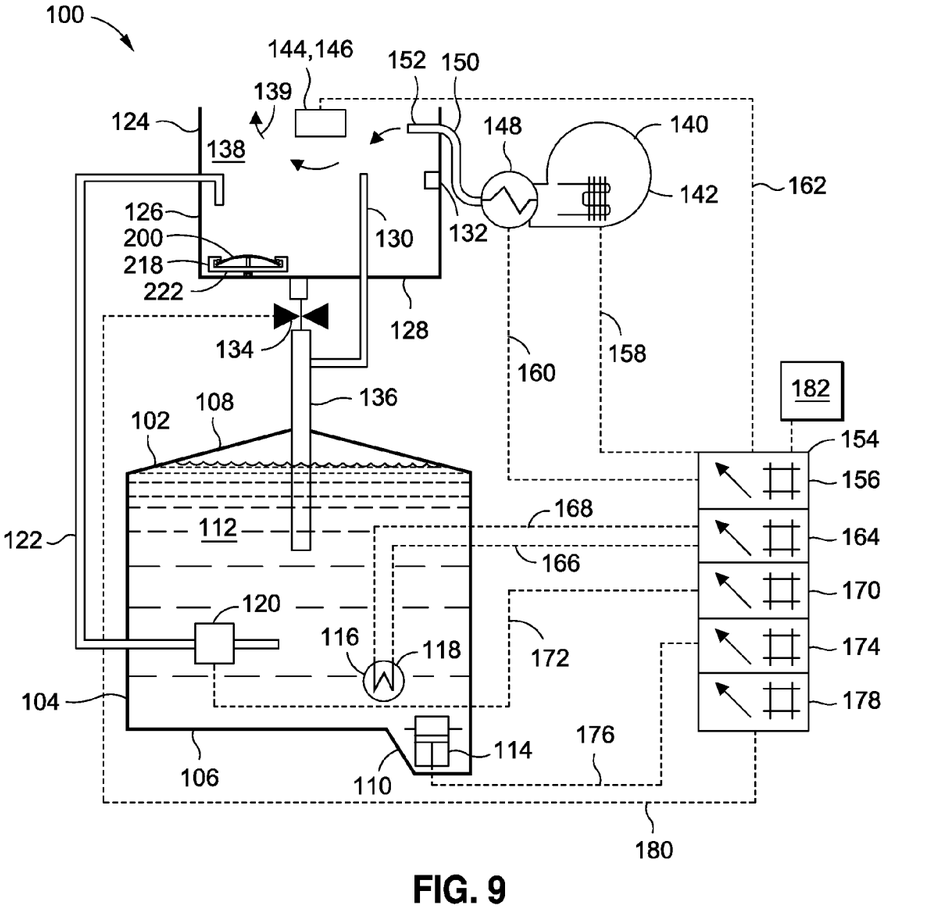
FIG. 9 is a schematic diagram of the testing apparatus illustrating the drying of the test specimen and the circulation of air in the test tank.

Step 312 of the method 300 of FIG. 5 may include draining the test tank 124 of solution 112 as shown in FIG. 8, and allowing the test specimen 200 to dry for a predetermined drying time period as shown in FIG. 9. For embodiments where the test specimen 200 is dried according to ASTM G-44, the drying time period may extend for 50 minutes of each hour±1 minute. In an embodiment, the method may include draining the test tank 124 by opening the drain valve 134 and allowing the solution 112 to flow through the drain pipe 136 by gravity feed back into the reservoir 102 as shown in FIG. 8. The test tank 124 may remain empty of solution 112 until the test specimen 200 is thoroughly dry.

Step 314 of the method 300 of FIG. 5 may include circulating the air 138 within the test tank 124. In an embodiment, the air 138 may be continuously circulated in the test tank 124 during the immersion time period and during the drying time period as shown in FIGS. 1 and 6-9. Drying of the test specimen 200 may be facilitated by the air circulation 139 in the test tank 124 as a result of conditioned air discharged from the air conditioning duct 150 into the test tank 124.

Step 316 of the method 300 of FIG. 5 may include controlling the air temperature and/or the relative humidity of the air 138 within the test tank 124. As indicated above, the air temperature and the relative humidity may be continuously controlled during the drying time period and the immersion time period by regulating the air conditioning system 140 and the inline duct heater fluidly coupled to the test tank 124. The method may include measuring the air temperature and the relative humidity of air 138 in the test tank 124 at predetermined intervals or continuously. The method may include measuring the air temperature of the air 138 in the test tank 124 using one or more tank thermocouples 144 that may be mounted in the test tank 124, and regulating the air temperature within a predetermined range (e.g., 27 C±1 C) using the air conditioning system 140. The method may additionally include measuring the relative humidity of the air 138 in the test tank 124 using one or more hydrometer s146 that may be mounted in the test tank 124, and regulating the relative humidity of the air 138 to within a predetermined range (e.g. 45%±10%) using the air conditioning system 140.

Step 318 of the method 300 of FIG. 5 may include recording the solution temperature, the air temperature, and/or the relative humidity of the air 138 within the test tank 124 during the immersion and drying cycles. The method may additionally include downloading recordings of the solution temperature, the air temperature, the relative humidity, and/or other test parameters, and charting the measurements of such test parameters on a display monitor (not shown).

The method may further include repetitively immersing the test specimen 200 and allowing the test specimen 200 to dry, and recording test parameter measurements for a predetermined period of time. For example, test parameter measurements may be recorded twenty-four (24) hours/day for a predetermined number of test days (e.g., for 10 days) as recommended for the type of material under test. In this regard, the duration of the testing procedure may be dependent upon the corrosion resistance of a given material in a corrosive environment.

Figure 4:
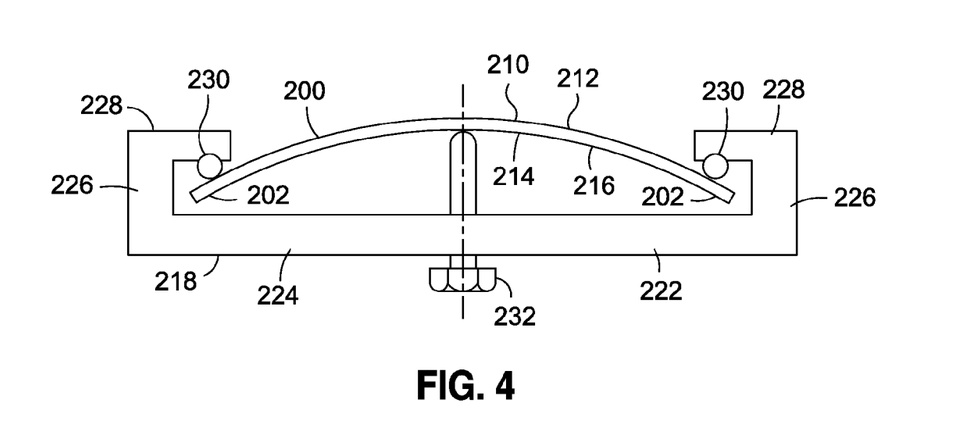
FIG. 4 is an illustration of a stressing fixture for inducing tensile stress in the test specimen during stress corrosion testing using the testing apparatus.

The method may further include inducing a sustained tensile stress 212 in the test specimen 200 using a stressing fixture 222. For example, FIG. 4 illustrates a stressing fixture 222 for inducing tensile stress 212 in an elongated test specimen 200 mounted to the stressing fixture 222. The stressing fixture 222 may be positioned within the test tank 124 after applying tensile stress 212 to the test specimen 200.

The method may further include monitoring the test specimen 200 for the formation of cracks at predetermined time intervals. For example, the method may include visually observing the test specimen 200 during testing such as by using a camera having magnification capability (e.g., 5-10 times magnification) that allows for detection of microcracking on the surface of the test specimen 200. Although not shown, such a camera may comprise a watertight camera mounted within the test tank 124 directly above the surface of the test specimen 200. The camera may be coupled to a display monitor outside of the test tank 124 capable of generating images recorded by the camera. Such images may be recorded on a periodic basis and may be displayed on the display monitor during the testing process.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. A testing apparatus, comprising
a reservoir configured to contain a solution;
a stationary test tank fluidly coupled to the reservoir and configured to contain a test specimen and receive the solution from the reservoir;
a fill pump configured to pump the solution from the reservoir to the test tank; and
a drain valve configured to drain the solution from the test tank and into the reservoir;
a sequence controller communicatively coupled to the fill pump and the drain valve and configured to provide sequence timing for the activation and deactivation of the fill pump and drain value to alternately fill and drain the test tank to alternately immerse the test specimen during an immersion time period and allow the test specimen to dry during a drying time for a repeated number of immersion and drying cycles, the sequence controller closing the drain valve after the test tank is drained of solution and maintaining the fill pump in a deactivated state during each drying time period prior to reactivating the fill pump for refilling the test tank to re-immerse the test specimen during each immersion time period.

2. The testing apparatus of claim 1, further comprising:
a circulation pump mounted in the reservoir for circulating the solution.

3. The testing apparatus of claim 1, further comprising:
a reservoir thermocouple mounted in the reservoir and configured to measure a solution temperature of the solution contained within the reservoir; and
a solution heater configured to maintain the solution within a desired solution temperature range.

4. The testing apparatus of claim 1, further comprising:
a fill pump controller configured to regulate the fill pump for pumping solution from the reservoir up to the test tank.

5. The testing apparatus of claim 1, further comprising:
an automatic fill switch configured to indicate a filled state of the test tank and send a signal to a controller for deactivating the fill pump.

6. The testing apparatus of claim 1, further comprising:
an air conditioning system configured to control an air temperature and a relative humidity of air in the test tank.

7. The testing apparatus of claim 6, wherein the air conditioning system includes:
a compressor fluidly coupled to the test tank;
a tank thermocouple mounted in the test tank and configured to measure the air temperature in the test tank;
a hydrometer mounted in the test tank and configured to measure the relative humidity of the air in the tank; and
an air heater fluidly coupled to the test tank and configured to heat the air in the test tank.

8. The testing apparatus of claim 1, further comprising:
a stressing fixture mountable in the test tank and configured to induce tensile stress in the test specimen.

9. A testing apparatus, comprising
a reservoir configured to contain a solution;
a stationary test tank fluidly coupled to the reservoir and positioned above the reservoir, the test tank being configured to contain a test specimen and receive the solution from the reservoir for immersion of the test specimen;
a fill pump configured to pump the solution from the reservoir up to the test tank;
a drain valve fluidly coupled to the test tank for draining the solution into the reservoir by gravity feed; and
a sequence controller communicatively coupled to the fill pump and the drain valve and configured to provide sequence timing for the activation and deactivation of the fill pump and drain value to alternately fill and drain the test tank to alternately immerse the test specimen during an immersion time period and allow the test specimen to dry during a drying time for a repeated number of immersion and drying cycles, the sequence controller closing the drain valve after the test tank is drained of solution and maintaining the fill pump in a deactivated state during each drying time period prior to reactivating the fill pump for refilling the test tank to re-immerse the test specimen during each immersion time period.

10. A method of stress corrosion testing of a test specimen, comprising:
(a) fixedly positioning a test specimen in a stationary test tank;
(b) pumping, using a fill pump activated by a sequence controller, a solution from a reservoir into the test tank;
(c) immersing the test specimen within the solution for an immersion time period;
(d) deactivating the fill pump and opening a drain valve using the sequence controller;
(e) draining the solution from the test tank;
(f) closing the drain valve using the sequence controller and maintaining the fill pump in a deactivated state after the test tank is drained of solution;
(g) allowing the test specimen to dry for a drying time period prior to reactivating, using the sequence controller, the fill pump for refilling the test tank to re-immerse the test specimen within the solution for the immersion time period;
(h) repeating steps (b) through (g) for a plurality of immersion and drying cycles.

11. The method of claim 10, wherein the step of deactivating the fill pump includes:
detecting, using an automatic fill switch, a level of the solution in test tank; and
stopping the pumping of solution into the test tank when the solution reaches a predetermined fill level.

12. The method of claim 10, further comprising:
circulating the solution in the reservoir using a circulation pump mounted within the reservoir.

13. The method of claim 10, further comprising:
measuring an air temperature in the test tank; and
regulating the air temperature using an air conditioning system fluidly coupled to the test tank.

14. The method of claim 10, further comprising:
measuring a relative humidity of air in the test tank; and
regulating the relative humidity of the air using an air conditioning system fluidly coupled to the test tank.

15. The method of claim 10, further comprising:
recording at least one of a solution temperature, an air temperature, and a relative humidity of the air within the test tank during immersion and drying cycles of the test specimen.

16. The method of claim 10, further comprising:
inducing a tensile stress in the test specimen using a stressing fixture.

17. The method of claim 10, further comprising:
visually observing the test specimen for a formation of cracks at predetermined time intervals.

* * * * *